United States Patent [19]

Psaledakis

[11] Patent Number: 4,514,388

[45] Date of Patent: Apr. 30, 1985

[54] PROTEOLYTIC ENZYMES IN THE ZYMOGEN FORM TO TREAT SARCOMA CELLS

[76] Inventor: Nicholas G. Psaledakis, 1296 Middlesex St., Lowell, Mass. 01852

[21] Appl. No.: 517,801

[22] Filed: Jul. 27, 1983

Related U.S. Application Data

[63] Continuation of Ser. No. 436,316, Mar. 22, 1983, abandoned.

[51] Int. Cl.$^3$ .................... A61K 37/54; A61K 37/547
[52] U.S. Cl. ...................................................... 424/94
[58] Field of Search ......................................... 424/94

[56] References Cited

PUBLICATIONS

Chem. Abst., 10th Coll., Chem. Subst. Index, vol. 86-95, (1977-1981) p. 54094cs.
Oliveira et al–Chem. Abst., vol. 93, (1980), p. 1490s.

*Primary Examiner*—Sam Rosen
*Attorney, Agent, or Firm*—Edward A. Gordon

[57] ABSTRACT

A method and composition is disclosed for the prophylactic treatment of cancer tumor cells contained in a host body having a natural immunological system and wherein the tumor cells have a protective surface resistant to the immunological system, to prevent or at least reduce further development of the tumor cells comprising; introducing a solution of a proenzyme and a pharmaceutically acceptable carrier into the host body adjacent the tumor cells, the solution having a concentration of the proenzyme at least in excess of the proenzymes produced by the host body in the area of the tumor cells, and contacting the tumor cells with the proenzyme whereby the proenzyme is converted to its active form which reacts with the tumor cell surface to sufficiently decompose the surface to permit the natural immunological system to prevent or reduce development of tumor cells.

3 Claims, No Drawings

PROTEOLYTIC ENZYMES IN THE ZYMOGEN FORM TO TREAT SARCOMA CELLS

This application is a continuation of application Ser. No. 436,316 filed Mar. 22, 1983, now abandoned.

FIELD OF THE INVENTION

This invention relates to a therapeutic composition in the regressive treatment of tumor cells. More particularly, the invention is directed to a proteolytic enzyme composition in which the enzyme is in the inactive or zymogen form employed therapeutically in the treatment of cancer tumor cells and to the method of treating cancer tumor cells in mammals.

BACKGROUND OF THE INVENTION

An enzyme is an organic catalyst produced by living cells but capable of acting independently. They are complex proteins which are capable of inducing chemical changes in other substances without being changed themselves in the process.

Enzymes are found particularly in digestive juices acting upon food substances, causing them to break down into simpler compounds. They are capable of accelerating greatly the speed of chemical reactions.

The reactions effected by the digestive enzymes are chiefly decompositions of a hydrolic nature, but enzymes are equally important in the synthetic reactions of assimilation.

The substance acted upon by an enzyme is called the substrate. Zymogen is the name given to the precursor of an enzyme. The more common groups of enzymes are: Hydrolytic enzymes; fat-, protein-, starch-, and sugar-splitting enzymes; coagulating enzymes or those which cause clotting, such as rennin or thrombin; oxidases or oxidizing enzymes deamidizing enzymes, those which are important in removing amines or amino groups during oxidation; reductases or reducing enzymes; splitting enzymes; joining enzymes, and those in the active form such as trypsin which promote clotting.

The physiological function of the proteolytic enzymes in digestion of proteins is well known, their action being to split proteins into amino acids and peptides. Hence they have long been administered orally for digestive purposes in cases of pancreatic deficiency, see example "Entozyme", Pacific Drug Review, July 1959, page 66, and Merck Index, 6th ediction, Merck & Co., Inc., Rahway, November 1952, page 981.

Proteolytic enzymes have been demonstrated to be effective therapeutics in reducing inflammation and edema when properly administered. It is theorized that trypsin functions as a depolymerase at the site of inflammation to reverse the fibrogen-fibrin reaction responsible for the inflammation. As the porosity of the protein network wall is increased, the intercellular fluid is released, hydrostatic pressures are reduced, capillaries open, and circulation in the local area is restored. Thus the anti-inflammatory action of trypsin is a direct result of its facilitating drainage from the inflamed area by lysis of fibrin plugs in the lymphatics and capillaries about the inflammatory lesion.

It is known that trypsin, chymotrypsin and some proteolytic enzymes can be administered intramuscularly and are effective in reducing inflammation. In U.S. Pat. No. 3,004,893 to Julius Martin, Oct. 12, 1961, there is disclosed an enteric coated trypsin and chymotrypsin anti-inflammatory composition which may be administered orally to obtain systemic absorption of these proteolytic enzymes from the ileum. The enteric coating is of such a composition that it will not break down until the tablet or capsule reaches the ileum. While such compositions are suitable as an anti-inflammatory treatment, they are not considered suitable for anti-tumor treatment.

U.S. Pat. No. 3,940,478 to Leonard D. Kirtz, Feb. 24, 1976, discloses the use of proteolytic enzymes in the active forms to facilitate contact of an antibiotic with the bacteria of a wound. As described therein the proteolytic enzyme works on the film of proteinaceous coagulum that the body tends to form on the surface of open wounds to disrupt or otherwise break it down thereby permitting access of the antibiotic to the shielded bacteria. While such method of utilizing proteolytic enzymes in their active form as adjuncts to antibiotics is suitable for topical applications to open wounds, such method is not disclosed as suitable for in vivo treatment of tumor cells.

One of the most distressing characteristics of cancer is the apparent failure of the body's immune system to combat the run-away tumor cells. The cancer tumor seems remarkably to elude, or delude, the natural defenses of immunological surveillance that manage to ward off most other diseases. It is believed that cancer tumors may avoid the body's normal defenses by growing a "protective shell" formed out of substances secreted by the growths themselves. Normally, the body's defense mechanism would recognize certain proteins, for example, on the surface of the tumor cells and attack them, but the protective shell made of a substance called fibrin gel gets in the way and may be the reason immunotherapy is limited. It is also believed that, ordinarily, when fibrin begins to form in tissue, as it would in healing, it attracts certain disease fighting cells. However, the cancerous tumor is believed to secrete another substance called microphage - migration inhibitor that wards off any cells destructive to the tumor. While little is known about the mechanisms by which tumor cells elude immunologic surveillance, it is desirable to provide a process of treating such tumors to render them susceptible to immunological surveillance, whereby regression is effected and/or tumor growth inhibited or reduced. It is also a desirable object to provide a therapeutic composition which will sufficiently decompose the shell of cancer tumors to permit the natural immunological system to take over.

SUMMARY OF THE INVENTION

The invention is based on the discovery that proteolytic enzymes when introduced in vivo in the host body in the inactive zymogen form, also known as the proenzyme form, in compositions having concentrations of the proenzyme greater than that produced by the body and brought into contact with the shell of fibrin gel of the cancer tumor and activators (co-enzyme for example) associated with the shell whereby the proenzyme is converted into its active form which then decomposes the tumor shell sufficiently to permit the host body's immunological system to take over.

DETAILED DESCRIPTION OF THE INVENTION

Proteolytic enzymes, also commonly referred to as proteinases or proteases are by definition enzyme compounds which hydrolyze, digest, depolymerize or otherwise degrade or decompose protein. Such proteolytic enzymes are trypsin, pepsin, rennin, chymotrypsin, pankrin, enterokinase, chymopapain, ficin, bromelin, B. subtilis proteinase, insulinase, aspergillus proteinase, carboxypeptidase, protaminase, asparaginase, cerevase and rapidase.

Illustrative of proenzymes suitable for use in the invention are the inactive of zymogen form of such proteolytic enzymes. For example, the proenzyme form of trypsin is trypsinogen and chymotrypsin is chymotrypsinogen. If desired, mixtures of proenzymes can be used.

While the mechanism of the process is not fully understood, it is believed that the proenzyme, trypsinogen is activated to trypsin by activators such as proteinkinases which are present on or associated with the tumor cell shells whereby the trypsin digests the coating shell permitting the normal immune system of the host to take over and destroy the cancerous cells. Excess active trypsin is neutralized by other enzymes present, such as alpha-1-antitrypsin.

The invention will now be further described by the following examples which are merely illustrative and should not be construed as limiting the invention in any way. The effect of the present invention is demonstrated in vivo by the experimental results of the following examples obtained using mice as the test animals.

The proenzymes employed in the following examples was trypsinogen, purchased commercially.

The trypsinogen was as follows:
Sigma Trypsinogen (T 9503)
Type I from bovine pancreas
1X recrystallised.
(Activity 8,000–10,000 BAEE units/mg protein ($E^1_2$ 80%) after activation to trypsin. May contain up to 1,000 BAEE units/mg protein prior to activation.

One BAEE unit = $\Delta A253$ od 0.001/minute with N$\alpha$-benzoyl-L-arginine ethyl ester (BAEE) as substrate at pH 7.6 at 25° C.: Reaction volume = 3.2 ml (1 cm lightpath).

The toxicity of the proenzyme was determined as follows:
Test solutions.
Trypsinogen 7.9 mg/ml in saline
The test solutions were stored at 2° C.
Toxicity test:

Groups of adult female (Charles River CD-1 strain, Wilmington, MA) mice were injected intraperitoneally (ip) with a single dose of the proenzyme in a volume of 0.5 ml saline. The drugs were administered at six dose levels, in about 2X step, based on the body weight of the test animals.

The animals were observed for 3 hours after the injection for sign of acute toxicity and at 24 hours while there were kept under standard laboratory conditions with water and food offered ad libidum.

The animals surviving the first 24 hours after treatment were subject for a second injection with the test solutions according to the previous schedule and observed for another 24 hours for toxic symptoms.

Explanation for Table 1
A = dose level or proenzyme
B = ml of test solution injected/mouse
If volume is less than 0.5 ml, saline was added to bring the volume of injection to 0.5 ml.

For dose levels 1, 2 and 3 the original test solution of 7.9 mg/ml trypsinogen was used.

For dose levels 4, 5 and 6 secondary stock solutions were made as follows: for trypsinogen 1.25 ml of test solution of 7.9 mg/ml was diluted to 10 ml with saline = 0.987 mg/ml trypsinogen.
C = mg drug injected/mouse
D = mean body weight of mouse in the group
E = drug administered in mg/kg mouse

TABLE 1

| | | Toxicity of trypsinogen: | | |
|---|---|---|---|---|
| A | B | C | D | E |
| 1 | 0.5 | 3.95 | 33.5 | 117.91 |
| 2 | 0.25 | 1.975 | 31.7 | 62.30 |
| 3 | 0.125 | 0.987 | 32.2 | 30.65 |
| 4 | 0.5 | 0.493 | 35.5 | 13.88 |
| 5 | 0.25 | 0.246 | 33.0 | 7.45 |
| 6 | 0.125 | 0.123 | 33.0 | 3.72 | mean body weight of animals at beginning of treatment: 3.15 ± 1.31 g
Results:

No acute toxicity was observed with the proenzyme at 24 hrs. (first injection) and at 48 hrs. (2nd injection).

All animals survived the treatment with the proenzyme and showed no body weight loss greater than the standard deviation at the beginning of the treatment.

The accumulated proenzyme received/mouse in two injection was:

| A | trypsinogen in mg/kg |
|---|---|
| 1 | 235.82 |
| 2 | 124.60 |
| 3 | 61.30 |
| 4 | 27.76 |
| 5 | 14.90 |
| 6 | 7.44 |

The amount of protein injected at the highest concentration, based on molecular weight of 25,000 daltons of the proenzyme was $9.432 \times 10^{-6}$ Mole for trypsinogen Intraperitoneal treatment of ascitic Sarcoma-180 cells with trypsinogen in mice.

EXAMPLE 1

Stock solutions:
Trypsinogen 7.92 mg/ml in saline
The solution was stored at 2° C.
Biological test:

Adult female CD-1 mice (Charles River, Wilmington, MA) were inoculated intraperitoneally (ip) with freshly collected ascitic fluid from donor animals (0.2 ml) containing Sarcoma 180 cells. Each animal received about 20 million cells in a volume of 0.2 ml of ascitic fluid. The cell viability of the inoculum was 98% estimated by the trypan blue exclusion test.

The donor animals for the inocculation were obtained from the Arthur D. Little company and carried 7 days old inocculum of generation number 33 of Sarcoma-180 cells.

The mice inoculated with the cancer cells were randomly assigned to treatment and control groups 24 hours after the inocculation and were kept under standard laboratory condition with water and food offered ad libidum.

The body weight of the mice in the treatment and control groups were measured daily and the mean weight of the animals in the groups were recorded.

The treatment of one intrapertitoneal injection of the proenzyme in a total volume of 0.5 ml/mouse/day started 24 hours after the inoculation with the tumor cells and continued for seven consecutive days. The injection was administered the same time of the day (between 2-3 P.M.) on each treatment days.

There were two dose levels of the drug as follows: Trypsinogen: (1) 0.5 ml of the stock solution of 7.92 mg/ml=3.92 mg of proenzyme with the initial mean body weight of 33.25 g;=119.09 mg/kg mouse. (2) 0.25 ml of stock solution of 7.92 mg mixed with 0.25 ml saline=1.98 mg of proenzyme with the initial body weight of 37.25 g;=53.15 mg/kg mouse.

The control groups (5) mean body weight of 33.00 g and (6) with mean body weight of 33.12 g received 0.5 ml saline at the same time, route and frequency.

Four animals were used for each drug level of the treatment groups and were compared to eight animals in the two control groups for the evaluation of the biological activity.

On the eighth day of treatment the animals were sacrificed by cervical dislocation, the ascitic fluid present in the abdominal cavity was collected, and the volume was recorded. Then the intraperitoneal cavity was washed (rinsed) out with 10 ml of saline. The washing was added to the collected ascitic fluid. The number of malignant cells present in the diluted ascites (ascites+rinse) was estimated by counting on an Autocytometer (Fisher Scientific Co.) at 1:250 fold dilution with Tuerk solution (1% acetic acid+traces of gential violet).

From the cell count the total number of cells present in the animals were calculated and the efficacy of the treatment was expressed as T/C% (the percent value of test over control), I% (inhibition) or P% (promotion).

Explanation of Table 3.
A=treatment day
B=survival of treatment (number of animals living-/number of animals at start)
C=mean body weight in grams
D=change of body weight from day one.

Explanation of Table 4.
A=survival of animals
B=ml ascites fluid collected
C=ml saline wash of abdominal cavity
D=total volume of ascites (diluted) in ml
E=number of tumor cells X10$^6$/ml ascites fluid
F=mean tumor cell number X10$^6$
G=total number of cells in ascites X10$^6$
H=tumor cell X 10$^6$/ml ascites fluid
I=T/C% (percent test/control)
J=I% (percent inhibition)
K=P% (percent promotion)

TABLE 3

Body weight change:
Trypsinogen:

| | 0.5 ml injection | | | 0.25 ml injection | | |
|---|---|---|---|---|---|---|
| A | B | C | D | B | C | D |
| 1 | 4/4 | 33.25 | — | 4/4 | 37.35 | — |
| 2 | 4/4 | 32.25 | −1.0 | 4/4 | 35.62 | −1.73 |
| 3 | 3/4 | 36.30 | +3.05 | 4/4 | 36.75 | −0.60 |
| 4 | 3/4 | 37.30 | +4.05 | 4/4 | 38.37 | +1.02 |
| 5 | 3/4 | 36.60 | +3.35 | 4/4 | 38.75 | −1.40 |
| 6 | 3/4 | 35.76 | +2.51 | 4/4 | 38.00 | +0.65 |
| 7 | 3/4 | 36.80 | +3.55 | 4/4 | 38.20 | +0.85 |

Controls:

| | 0.5 ml saline | | | 0.5 ml saline | | |
|---|---|---|---|---|---|---|
| A | B | C | D | B | C | D |
| 1 | 4/4 | 33.00 | — | 4/4 | 33.12 | — |
| 2 | 4/4 | 32.25 | −0.75 | 4/4 | 32.75 | −0.37 |
| 3 | — | — | — | — | — | — |
| 4 | — | — | — | — | — | — |
| 5 | — | — | — | — | — | — |
| 6 | 4/4 | 38.00 | +5.00 | 4/4 | 38.75 | +5.45 |
| 7 | 4/4 | 38.37 | +5.37 | 4/4 | 39.00 | +5.88 |

TABLE 4

Evaluation of the efficacy of proenzyme treatment on the development of intraperitoneal Sarcoma-180 cells in mice.

| Treatment | A | B | C | D | E | F | G | H | I | J | K |
|---|---|---|---|---|---|---|---|---|---|---|---|
| Control (5) | 4/4 | 5 | 10 | 15 | 8.7, 8.8 | 8.75 | 131.25 | | | | |
| | | 4 | 10 | 14 | 16.0, 16.0 | 16.0 | 224.00 | | | | |
| | | 6 | 10 | 16 | 22.0, 22.6 | 22.4 | 334.00 | | | | |
| | | 6 | 10 | 16 | 18.2, 18.2 | 28.2 | 292.00 | 1062 | 100 | 0 | 0 |
| Control (6) | | 5 | 10 | 15 | 17.0, 17.0 | 17.0 | 225.00 | 19 | | | |
| | | 4 | 10 | 14 | 23.0, 23.0 | 23.0 | 322.00 | | | | |
| | | 5 | 10 | 15 | 21.0, 21.0 | 21.0 | 315.00 | | | | |
| | | 3 | 10 | 13 | 19.6, 19.2 | 19.4 | 252.00 | | | | |
| Trypsinogen (1) 119.09 mg/kg | 3/4 | 7 | 10 | 17 | 15.2, 12.0 | 15.1 | 255.00 | | | | |
| | | 3 | 10 | 13 | 12.8, 12.8 | 12.8 | 166.40 | 490.8 | 47.17 | 53.8 | — |
| | | 1 | 10 | 11 | 5.8, 5.9 | 5.85 | 69.40 | 11 | | | |
| Trypsinogen (2) 53.15 mg/kg | 4/4 | 4 | 10 | 14 | 5.3, 5.3 | 5.3 | 72.20 | | | | |
| | | 0.5 | 10 | 10.5 | 2.8, 2.7 | 2.75 | 28.35 | 205.15 | 19.30 | 80.7 | — |
| | | 6 | 10 | 16 | 4.9, 4.9 | 4.85 | 77.60 | 15.5 | | | |
| | | 5 | 10 | 15 | 1.8, 1.8 | 1.8 | 27.00 | | | | |

EXAMPLE 2

The intrapertioneal treatment of ascitic tumor cells at 50 mg/kg dose level of the proenzymes.

Proenzyme stock solution:
Trypsinogen: 11.51 ml of 7.92 mg/ml of trypsinogen solution was diluted with saline to 30 ml=3.057 mg of proenzyme/ml =1.528 mg proenzyme/0.5 ml Biological test:
The same general protocoll was used as described before, except the mice were 8 weeks old and were inoculated with an ascitic fluid collected freshly from donor animals that contained 54×10$^6$ Sarcome-180 cell/0.1 ml inocculum.

Six animals were used for each test and results was compared to 10 mice in the control group.

Explanation of Table 5
A=treatment day
B=survival of treatment
C=mean body weight of mice in grams
D=change of body weight from day one in grams Explanation of Table 6
A = survival
B = total volume of ascites (diluted) in ml (containing ascites fluid and washing of abdominal cavity)
C = mean tumor cell number $\times 10^6$/ml diluted ascitic fluid
D = cell yield $\times 10^6$/mice (calculated from mean values of E)
E = total cell number in ascitic fluid (diluted) $\times 10^6$
F = T/C%
G = I%

TABLE 5

| Body weight change of experimental animals during treatment. | | | | | | |
|---|---|---|---|---|---|---|
| Treatment | Control | | | TRYPSINOGEN | | |
| A | B | C | D | B | C | D |
| 1 | 10/10 | 29.9 | — | 6/6 | 30.21 | — |
| 2 | — | — | — | 6/6 | 29.40 | −0.81 |
| 3 | — | — | — | 6/6 | 30.88 | +0.62 |
| 4 | — | — | — | 6/6 | 31.28 | +1.07 |
| 5 | 10/10 | 33.74 | +3.84 | 6/6 | 30.78 | +0.57 |
| 6 | 10/10 | 33.9 | +4.0 | 6/6 | 31.50 | +1.29 |

TABLE 6

| Evaluation of the efficacy of Sarcoma-180 treatment at 50 mg/kg proenzyme level in mice. | | | | | | | |
|---|---|---|---|---|---|---|---|
| Treatment | A | B | C | D | E | F | G |
| Control: | 10/10 | 18,18,17 14,18,17 18,15,19 17 | 24,12,12.6 15.2,11,15 20.2,19,19.4 19.6 | 432,216,214.2 218.8,198,255 363.6,205,368.6 332.2 | 287.84 | 100 | 0 |
| Trypsinogen: | 6/6 | 15,16,13 14.5,13,15 | 14.4,7.5,3.6 2.5,9.16 | 216,120,46.8 36.25,117,240 | 129.34 | 49.93 | 55.6 |

The data of Tables 4 and 6 show that the trypsinogen inhibited the development of Sarcoma-180 cells in vivo. The benefits of trypsinogen were most apparent in dose levels of 53.15 mg/kg which resulted in 80.7% inhibitory effect as shown on Table 4. The results of the tests show that proenzymes have significant therapeutic value in the prophylatic treatment of cancer tumor cells.

While the invention has been described with respect to preferred embodiment it will be apparent to those skilled in the art that changes and modifications may be made without departing from the scope of the invention herein involved in its broader aspects. Accordingly, it is intended that all matter contained in the above description, or shown in the accompanying drawing shall be interpreted as illustrated and not in limiting sense.

What is claimed is:

1. A method for the prophylatic treatment of sarcoma cancer tumor cells in a host body to prevent or at least reduce further development of said tumor cells comprising contacting said tumor cells with a proenzyme selected from the group consisting of trypsinogen, chymotrypsinogen and mixtures thereof in a concentration at least in excess of said proenzymes produced by the host body in the area of said tumor cells.

2. A method for the prophylatic treatment of sarcoma cancer tumor cells contained in a host body having a natural immunological system, said tumor cells having a protective surface resistant to said immunological system, to prevent or at least reduce further development of said tumor cells comprising: introducing a solution comprising a proenzyme selected from the group consisting of trypsinogen, chymotrypsinogen and mixtures thereof and a pharmaceutically acceptable carrier into the host body adjacent said tumor cells, said solution having a concentration of the proenzyme at least in excess of said proenzymes produced by the host body in the area of said tumor cells, and contacting said tumor cells with said proenzyme whereby the proenzyme is converted to its active form and reacts with said tumor cell surface to sufficiently decompose said surface whereby permitting said natural immunological system to reduce said tumor cells.

3. The method of claim 2 wherein the pharmaceutical carrier is a saline or water solution.

* * * * *